United States Patent
Yu et al.

(10) Patent No.: US 10,067,304 B2
(45) Date of Patent: Sep. 4, 2018

(54) FLUID COOLED OPTICAL FIBER

(71) Applicant: Boston Scientific Scimed, Inc., Maple Grove, MN (US)

(72) Inventors: Honggang Yu, San Jose, CA (US); Rongwei Jason Xuan, Fremont, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 15/847,650

(22) Filed: Dec. 19, 2017

(65) Prior Publication Data
US 2018/0172931 A1 Jun. 21, 2018

Related U.S. Application Data

(60) Provisional application No. 62/436,530, filed on Dec. 20, 2016.

(51) Int. Cl.
| | |
|---|---|
| *G02B 6/42* | (2006.01) |
| *G02B 23/24* | (2006.01) |
| *A61B 18/22* | (2006.01) |
| *A61B 18/26* | (2006.01) |
| *A61B 18/00* | (2006.01) |

(52) U.S. Cl.
CPC ............ *G02B 6/4251* (2013.01); *A61B 18/22* (2013.01); *G02B 23/2453* (2013.01); *A61B 18/26* (2013.01); *A61B 2018/00023* (2013.01); *A61B 2018/00035* (2013.01); *A61B 2018/2244* (2013.01); *G02B 6/4268* (2013.01)

(58) Field of Classification Search
None
See application file for complete search history.

(56) References Cited

U.S. PATENT DOCUMENTS

| | | | | |
|---|---|---|---|---|
| 5,304,171 A | * | 4/1994 | Gregory | A61B 18/245 385/125 |
| 5,496,307 A | * | 3/1996 | Daikuzono | A61B 18/24 606/15 |
| 5,785,704 A | * | 7/1998 | Bille | A61B 18/24 600/108 |
| 6,039,728 A | * | 3/2000 | Berlien | A61N 5/0601 606/15 |
| 9,757,198 B2 | * | 9/2017 | Griffin | A61B 18/20 |
| 9,770,294 B2 | * | 9/2017 | Brannan | A61B 18/1815 |

(Continued)

FOREIGN PATENT DOCUMENTS

WO WO 2016/148718 A1 9/2016

OTHER PUBLICATIONS

International Search Report and Written Opinion in PCT/US2017/067416, dated Apr. 24, 2018 (13 pages).

*Primary Examiner* — Jerry Rahll
(74) *Attorney, Agent, or Firm* — Bookoff McAndrews, PLLC

(57) ABSTRACT

Fluid cooled optical fibers are disclosed. An exemplary fiber comprises a fiber body including a distal end, an inner cap surrounding said distal end, an outer cap surrounding said inner cap, and a tube attached to said outer cap. The tube and outer cap may define a first flow channel, the outer and inner caps may define a second flow channel, and the outer cap may including one or openings for placing the first flow channel in communication with the second flow channel. Associated systems also are disclosed.

20 Claims, 2 Drawing Sheets

(56) References Cited

U.S. PATENT DOCUMENTS

| | | | |
|---|---|---|---|
| 9,888,964 B2* | 2/2018 | Hanley | A61B 18/24 |
| 9,937,003 B2* | 4/2018 | Brannan | A61B 18/1815 |
| 2003/0199860 A1* | 10/2003 | Loeb | A61B 18/24 |
| | | | 606/17 |
| 2005/0131399 A1* | 6/2005 | Loeb | A61B 18/24 |
| | | | 606/15 |
| 2006/0217693 A1* | 9/2006 | Gowda | A61N 5/0601 |
| | | | 606/15 |
| 2006/0282068 A1* | 12/2006 | Griffin | A61B 18/22 |
| | | | 606/13 |
| 2011/0118715 A1* | 5/2011 | Zerfas | A61B 18/22 |
| | | | 606/15 |
| 2012/0157982 A1 | 6/2012 | Anderson et al. | |
| 2014/0121655 A1* | 5/2014 | Chia | A61B 18/22 |
| | | | 606/16 |
| 2014/0309627 A1* | 10/2014 | Hanley | A61B 18/24 |
| | | | 606/15 |
| 2015/0011985 A1* | 1/2015 | Peng | A61B 18/22 |
| | | | 606/15 |
| 2017/0128133 A1* | 5/2017 | Pinnow | A61B 18/22 |
| 2018/0049806 A1* | 2/2018 | Yu | A61B 18/22 |

\* cited by examiner

FLUID COOLED OPTICAL FIBER

CROSS-REFERENCE TO RELATED APPLICATIONS

This application claims the benefit of priority to U.S. Provisional Application No. 62/436,530, filed Dec. 20, 2016, which is incorporated by reference herein in its entirety.

TECHNICAL FIELD

Aspects of the present disclosure generally relate to optical fibers. Particular aspects relate to a fluid cooled optical fiber.

BACKGROUND

Liquid cooled optical fibers may be used in laser systems to provide fast and efficient discharge of laser energy. Some liquid cooled fibers may include a single, continuous flow channel for directing a cooling liquid (e.g., water) about the fiber and/or a distal cap of the fiber. The interface between the optical fiber, tube, and distal cap is a known problem area. For example, gradual loosening of the distal cap is a known problem. Cap loosening may occur when the distal cap becomes moveable relative to the laser fiber because of heat generated from the laser energy. A loose cape failure occurs when some portion of the cap moves into the laser energy, generating even more heat. To avoid loose cap failure, many liquid cooled fibers are replaced prematurely, adding expense. Cap failure may also occur during a procedure, requiring the surgeon expend additional operation time, adding even more expense. The present disclosure addresses these problems and other deficiencies in the prior art.

SUMMARY

Aspects of the present disclosure relate to a fluid cooled optical fiber. Numerous aspects of the present disclosure are now described.

One aspect of this disclosure is an optical fiber. The fiber may comprise: an fiber body including a distal end with a reflective surface angled to direct laser energy out of the body along a laser axis; an inner cap surrounding the distal end of the fiber body, the inner cap including a proximal end attached to the fiber body, and at least one transmission portion aligned with the laser axis; an outer cap surrounding the inner cap, the outer cap including a proximal end attached to at least one of the inner cap and the fiber body, and an exit port aligned with the laser axis; and a tube surrounding at least portion of the fiber body, the tube including a distal end attached to the outer cap. According to this aspect, the tube and the outer cap may define a first flow channel, the outer cap and the inner cap may define a second flow channel, the outer cap may include one or more openings configured to place the first flow channel in communication with the second flow channel, and/or the one or more openings may be distal of the proximal end of the inner cap.

In some aspects, the proximal end of the inner cap may be attached to the fiber body by a first epoxy. The proximal end of the inner cap may include a surface feature configured to promote adhesion with the first epoxy. An interior surface of the inner cap may be spaced part from an exterior surface of the fiber body by the first epoxy to define a sealed interior cavity within the inner cap. The sealed interior cavity may include an insulative element. The optical fiber may further comprise one or more attachment points between the interior surface of the inner cap and an exterior surface of the distal end of the fiber body. The proximal end of the outer cap may be attached to the inner cap and by a second epoxy. The first epoxy may have a property different than that of the second epoxy. The second epoxy may encapsulate the proximal end of the inner cap and an exterior surface of the first epoxy. Similar to above, the proximal end of the inner cap may include a surface feature configured to promote adhesion with the second epoxy.

The one or more openings of the outer cap may be proximal of the exit port. In some aspects, the one or more openings may be positioned oppositely about the fiber body. A distal portion of the first flow channel may converge toward the one or more openings, and/or the second flow channel may include an expanded interior portion adjacent the exit port. In any of these aspects, the inner cap may be made of a glass and the outer cap is may be made of a metal.

Another aspect is an optical fiber tip comprising: an inner cap including an interior cavity sized to receive an optical fiber, a proximal end engageable with the optical fiber, and at least one transmission portion; and an outer cap including an interior cavity sized to receive the inner cap, a proximal end engageable with at least one of the inner cap and the optical fiber, an exit port, and one more openings. According to this aspect, when the inner and outer cap are coupled together, the at least one transmission portion may be aligned with the exit port, the outer cap and the inner cap may form a flow channel, and the one or more openings may be distal of the proximal end of the inner cap.

According to this aspect, the one or more openings may extend along an opening axis transverse with the fiber body. The second flow channel may include an expanded interior portion adjacent the exit port. The proximal end of the inner cap may be coupled to the proximal end of the outer cap by an epoxy. In other aspects, the inner cap may have a thermal resistance greater than a thermal resistance of the outer cap.

Yet another aspect of this disclosure is a laser system including an optical fiber, a laser source, and a fluid source. According to this aspect, the optical fiber may comprise: a fiber body extending between a proximal end engageable with a laser source and a distal end configured to direct laser energy out of the fiber body; an inner cap surrounding the distal end of the fiber body, the inner cap including a proximal end attached to the fiber body and at least one transmission portion; an outer cap surrounding the inner cap, the outer cap including a proximal end attached to the inner cap, and an exit port; a tube surrounding at least a portion of the fiber body, the tube including a proximal end engageable with a fluid source and a distal end attached to the outer cap; a first flow channel between the tube and the fiber body; a second flow channel between the outer cap and the inner cap; and one or more openings extending through the outer cap to place the first flow channel in communication with the second flow channel, each of the one or more openings being distal of the proximal end of the inner cap.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows.

DETAILED DESCRIPTION

Aspects of the present disclosure are now described with reference to a fluid cooled optical fiber. Some aspects are described with reference to medical procedures where laser energy is used to treat a kidney stone. References to a particular type of procedure, laser energy, stone object, and/or bodily organ are provided for convenience and not intended to limit the present disclosure unless claimed. Accordingly, the concepts described herein may be utilized for any analogous fiber—medical or otherwise, kidney-specific or not.

Numerous axes and directions are described. Each axis may be transverse, or even perpendicular, with the next so as to establish a Cartesian coordinate system with an origin point O. One axis may extend along a longitudinal axis of an element. Directions may be indicated by the terms "proximal" and "distal," and their respective initials "P" and "D," either of which may be used to describe relative components and features in relation to any axis described herein. Proximal refers to a position closer to the exterior of the body or a user, whereas distal refers to a position closer to the interior of the body or further away from the user. Appending the initials "P" or "D" to an element number signifies a proximal or distal location, and appending P or D to an arrow in a figure signifies a proximal or distal direction along one or more axes. Unless claimed, these terms are provided for convenience and not intended to limit the present disclosure to a particular location, direction, or orientation.

The term "generally" is used to indicate a range of possible values. For example, a laser axis L-L is described as being generally transverse with a fiber axis F-F, meaning that axis L-L may be transverse with or perpendicular to axis F-F. The term "generally" also may be synonymous with other descriptive terms, such as "about," "substantially," and/or "approximately," any of which may indicate a range of possible values that are within +/−5% of a stated value.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements.

Figure 1:
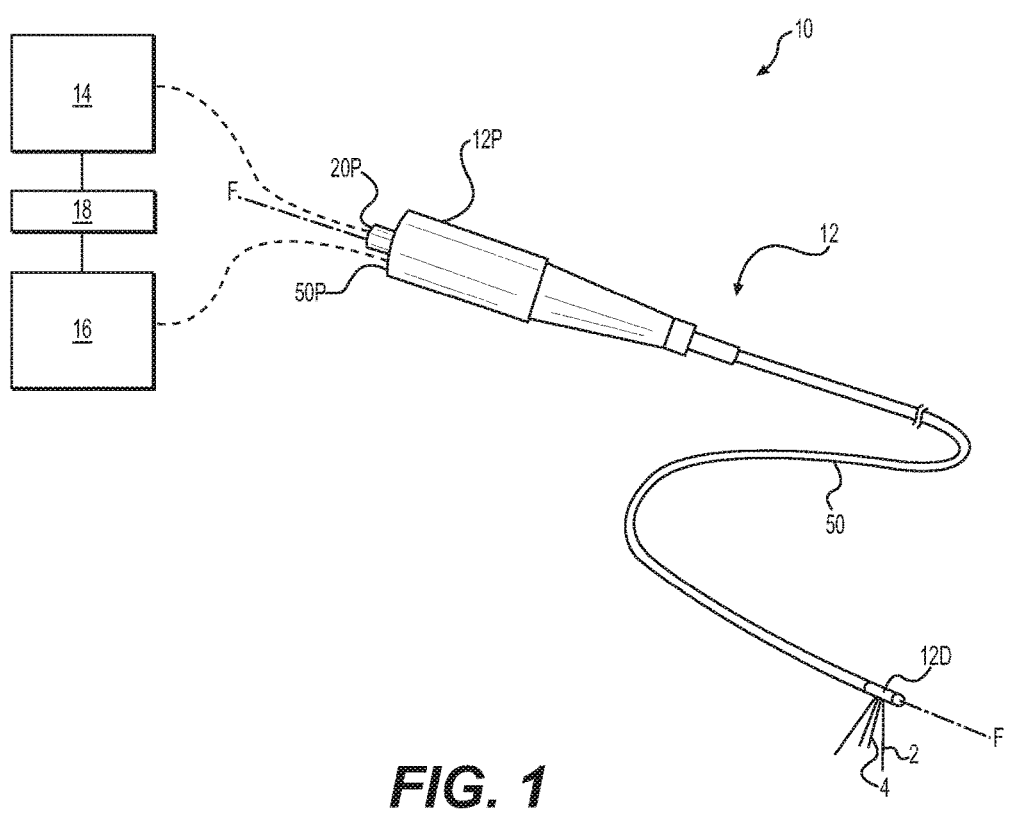
FIG. 1 depicts an optical fiber coupled to a fluid source and a laser source according to aspects of this disclosure.

One aspect of the present disclosure is depicted in FIG. 1 as a system 10. As shown, system 10 may comprise: a fluid cooled optical fiber 12; a laser source 14; a fluid source 16; and a controller 18. Optical fiber 12 includes a proximal end 12P coupled with laser source 14 and a fluid source 16, and a distal end 12D configured to discharge a laser energy 2 from laser source 14 and/or a fluid 4 from fluid source 16. Laser source 12 and/or fluid source 14 of FIG. 1 may, for example, be configured to discharge laser energy 2 and/or fluid 4 at the same or different times responsive to a control signal from controller 18.

Figure 2:
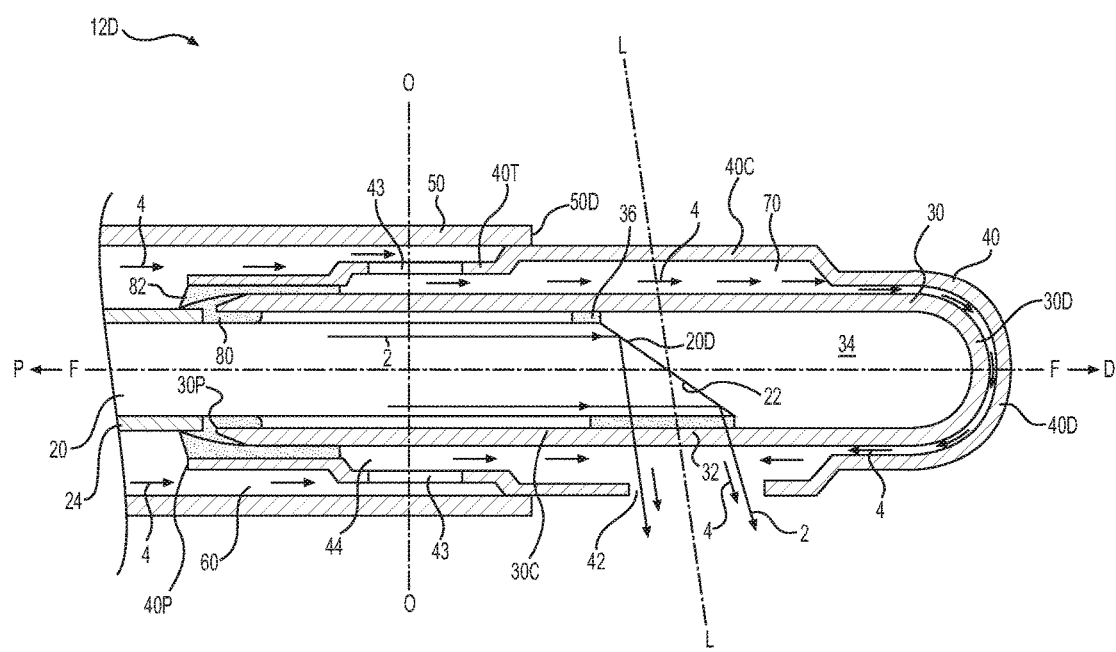
FIG. 2 depicts an optical fiber according to aspects of this disclosure.

An exemplary distal end 12D of optical fiber 12 is depicted in FIGS. 1 and 2. As shown, optical fiber 12 may comprise a fiber body 20 including a distal end 20D; an inner cap 30 surrounding distal end 20D; an outer cap 40 surrounding inner cap 30; and a tube 50 extending proximally from outer cap 40. According to this aspect, tube 50 and outer cap 40 may define a proximal or first flow channel 60; outer cap 40 and inner cap 30 may define a distal or second flow channel 70; and outer cap 40 may be configured to place proximal channel 60 in communication with distal channel 70. Within system 10, fluid 4 (e.g., carbon dioxide or saline) may be circulated through the proximal and distal channels 60 and 70 by fluid source 16.

As shown in FIGS. 1 and 2, fiber body 20 extends along a fiber axis F-F between distal end 20D and a proximal end 20P that is optically coupled to laser source 14. Distal end 20D of FIG. 2 has a side-fire configuration including a reflective surface 22 angled to direct laser energy 2 out of fiber body 20 along a laser axis L-L that is generally transverse with fiber axis F-F. Distal end 20D may alternatively have an end-fire configuration, wherein surface 22 is either omitted or further modified do direct laser energy 2 out distal end 20D so that laser axis L-L is generally parallel with fiber axis F-F. In FIG. 2, a proximal portion of fiber 20 of FIG. 2 includes a cladding 24, whereas a distal portion of fiber 20 does not. Cladding 24 may, for example, have a lower index of refraction than fiber body 20, retaining more of laser energy 2 in fiber body 20. Proximal end 20P may be optically coupled to laser source 14 by any conventional means.

In FIG. 2, inner cap 30 surrounds distal end 20D of fiber body 20. As shown, inner cap 30 may comprise: a proximal end 30P attached to fiber body 20; a central portion 30C including at least one transmission portion 32 aligned with the laser axis L-L; a distal end 30D; and an interior cavity 34 extending between distal end 30D and proximal end 30P. Each element of inner cap 30 is now described.

Proximal end 30P of inner cap 30 may be attached to fiber body 20 by a first epoxy 80. In FIG. 2, first epoxy 80 is configured to fix the position of inner cap 30 relative to fiber body 20, and/or seal interior cavity 34. For example, first epoxy 80 may be a first epoxy (e.g., a UV cured epoxy). In FIG. 2, first epoxy 80 covers proximal end 30P of inner cap 30 and a distal portion of cladding 24, providing a gradual transition between cap 30 and body 20. One or more surface features may be provided on fiber body 20, cladding 24, and/or cap 30 to promote adhesion with first epoxy 80. For example, the exterior or interior surfaces of the proximal end 30P of inner cap 30 may include surface features configured to promote adhesion with first epoxy 80. Exemplary surface features may include ridges, indentations, protrusions, threads, or like elements configured to provide an expanded surface area engageable with epoxy 80. The exterior surface of fiber body 20 may have complimentary surface features.

Central portion 30C includes at least one transmission portion 32 configured to pass laser energy 2 therethrough. Interior cavity 34 is sized to receive fiber body 20 so that laser axis L-L is aligned with transmission portion 32. For example, as shown in FIG. 2, inner cap 30 may be composed entirely of a transmission material (e.g., glass) having a constant diameter along fiber axis F-F. In this configuration, laser axis L-L may be aligned with transmission portion 32 in any position where laser energy 2 may be directed through portion 32 from reflective surface 22. According to other aspects, inner cap 30 may be composed of a non-transmission element (e.g., metal) with a variable diameter, and the at least one transmission portion 32 may include a separate transmission material attached to cap 30. In this configuration, laser axis L-L may be aligned with transmission portion 32 in any position where laser energy 2 may be directed through said transmission material from reflective surface 22. However formed, inner cap 30 and at least one transmission portion 32 may provide a continuous exterior surface of cap 30, allowing interior cavity 34 to be sealed off from channels 60 and 70.

First epoxy 80 may be configured to maintain a separation between the interior surface of inner cap 30 and the exterior surface of fiber body 20. First epoxy 80 may seal interior cavity 34. Once sealed, an insulative element (e.g., an insulating gas) may be placed inside of cavity 34. As shown in FIG. 2, for example, an attachment point 36 may be positioned inside cavity 34 and shaped to surround and/or support at least a portion of distal end 20D of fiber body 20. The attachment point 36 may be formed with a laser energy. For example, inner cap 30 may be made of a first material, and outer cap 40 may formed of a second material, such that a portion of caps 30 and 40 may be fused together with the laser energy (e.g., from a $CO_2$ laser) to define attachment point 36. Laser energy 2 may pass through attachment point 36 or an opening formed therein along laser axis L-L. According to some aspects, attachment point 36 may divide interior cavity 34 into a proximal sealed portion and a distal sealed portion, allowing different insulative elements to be provided in each sealed portion; or the same element to flow therebetween under direction of heat. Additional attachment points 36 may be formed between cap 30 and 40. Similar points 36 may be formed with first epoxy 80.

In FIG. 2, the interior and exterior surfaces of distal end 30D have semi-spherical surfaces that are coaxial with fiber axis F-F. The interior semi-spherical surface of distal end 30D may include a coating that directs laser energy 2 back towards fiber body 20, while the exterior semi-spherical surface of distal end 30D may be configured to direct fluid 4 back into distal cavity 70, as described below.

Outer cap 40 of FIG. 2 surrounds inner cap 30. Cap 40 may comprise: a proximal end 40P attached to inner cap 30; a transfer portion 40T including one or more openings 43; a central portion 40C including an exit port 42 aligned with laser axis L-L; a distal end 40D; and an interior cavity 44 extending between ends 40D and 40P. The elements of cap 60 are now described.

Proximal end 40P may be attached inner cap 30 by a second epoxy 82. In FIG. 2, second epoxy 82 is configured to fix the position of outer cap 40 relative to inner cap 30, and/or further seal interior cavity 34. The interior diameter of proximal end 40P of cap 40 may be sized relative to the outer diameter of proximal end 30P of cap 30. Second epoxy 82 may have at least one property that is the same or different than that of first epoxy 80. For example, first epoxy 80 may have a thermal resistance and/or elastic modulus greater than that of second epoxy 82. In some aspects, second epoxy 82 may be UV cured epoxy. First and second epoxies 80 and 82 may be cured by any other means, or be the same material.

In FIG. 2, second epoxy 82 covers proximal end 30P of inner cap 30 and the entirety of first epoxy 80, such that only epoxy 82 is exposed to fluid 4. One or more surface features may be provided on inner cap 30 and/or outer cap 40 to promote adhesion with second epoxy 82. For example, the interior surfaces of the proximal end 30P of inner cap 30 may include surface features (e.g., ridges) configured to promote adhesion with second epoxy 82. The interior surfaces of outer cap 40 and/or the exterior surfaces of first epoxy 80 may include similar surface features. Much like first epoxy 80, second epoxy 82 may be configured to maintain a separation between the interior surface of outer cap 40 and the exterior surface of inner cap 30. First epoxy 80 may be chemically or physically bonded with second epoxy 82 to further maintain this separation. For example, first epoxy 80 may be formulated to meld with second epoxy 82 under application of heat.

Transfer portion 40T includes one or more openings 43 extending through outer cap 40. The inner and outer diameters of transfer portion 40T are sized to direct fluid 4 into openings 43. Each opening 43 is, for example, located distal of proximal end 40P of outer cap 40, and proximal of a distal end 50D of tube 50. Openings 43 may be any shape (e.g., circles, ovals, and the like); and size (e.g., the same or different sizes). In FIG. 2, outer cap 40 includes at least two openings 43 configured to direct fluid 4 from proximal channel 60 into distal channel 70. Any number of openings 43 may be provided. These at least two openings 43 may, as in FIG. 2, be arranged oppositely along an opening axis O-O that is transverse or perpendicular with fiber axis F-F.

Central portion 40C includes exit port 42. Interior cavity 44 is sized to receive inner cap 30 so that both the exit port 42 of outer cap 40 and the at least one transmission portion 32 of inner cap 30 are aligned with laser axis L-L. In FIG. 2, exit port 42 is a through-hole that extends completely through outer cap 40, and is configured to discharge laser energy 2 and/or fluid 4 along laser axis L-L. Said through-hole may, for example, be coaxial with laser axis L-L. The diameter of interior cavity 44 at central portion 40C is expanded so as to permit attachment with tube 50, and concentrate a greater amount of fluid 4 adjacent exit port 42, where a majority of the heat may be generated. Exit port 42 may be configured to focus or dissipate fluid 4.

In FIG. 2, the interior and exterior surfaces of distal end 40D have semi-spherical surfaces coaxial with fiber axis F-F. Distal end 40D may be sized relative to distal end 30D of cap 30. For example, in FIG. 2, the interior semi-spherical surface of distal end 40D of outer cap 40 may be slightly larger than and spaced apart from the exterior semi-spherical of distal end 30D of inner cap 30, defining a return portion of distal flow channel 70.

As shown in FIG. 2, tube 50 may surround proximal portions of fiber body 20, inner cap 30, and/or outer cap 40. Any type of tubing be used. A distal 50D of tube 50 may be attached to central portion 40C of outer cap 40 at a location distal of one or more openings 43 by any conventional means. As shown in FIG. 1, a proximal end 50P of tube 50 may be engageable with fluid source 16 and configured to direct fluid 4 through first channel 60. Any type of fluid source may be used.

Proximal and distal flow channels 60 and 70 may be defined by fiber body 20, inner cap 30, outer cap 40, and/or tube 50. For example, in FIG. 2, an interior surface of tube 50 is spaced apart from an exterior surface of fiber body 20 so that proximal flow channel 60 is defined by tube 50 and body 20 as having an annular cross-section about fiber axis F-F. A distal portion of proximal flow channel 60 is configured to direct fluid 4 through transfer portion 40T. The pressure of fluid 4 may be increased in this configuration. For example, as shown in FIG. 2, the interior diameter of tube 50 may be constant, while the outer diameter of distal end 40D may be less than the outer diameter of transfer portion 40T, defining a funnel configured to increase the pressure of fluid 4 as it passes from channel 60 into channel 70.

As noted above, central portion 40C is sized to concentrate a greater amount of fluid 4 adjacent exit port 42. The interior surfaces of central portion 40C may be configured to direct fluid 4 out of exit port 42 and/or into the return portion of distal flow channel 70. For example, the interior surfaces of transfer portion 40T may include grooves (or like surface features) configured to direct a first portion of fluid 4 out of exit port 42, and second portion of fluid 4 into said return portion. A first set of grooves may, for example, be spiraled about the interior of central portion 40C to circulate a portion of fluid 4 around port 42, while a second set of grooves may extend along fiber axis F-F to circulate another portion of fluid 4 through the return portion of distal channel 70.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. An optical fiber comprising:
   an fiber body including a distal end including a reflective surface angled to direct laser energy out of the body along a laser axis;
   an inner cap surrounding the distal end of the fiber body, the inner cap including a proximal end attached to the fiber body, and at least one transmission portion aligned with the laser axis;
   an outer cap surrounding the inner cap, the outer cap including a proximal end attached to at least one of the inner cap and the fiber body, and an exit port aligned with the laser axis; and
   a tube surrounding at least a portion of the fiber body, the tube including a distal end attached to the outer cap,
   wherein the tube and the outer cap define a first flow channel, the outer cap and the inner cap define a second flow channel, the outer cap includes one or more openings configured to place the first flow channel in communication with the second flow channel, and the one or more openings are distal of the proximal end of the inner cap.

2. The optical fiber of claim 1, wherein the proximal end of the inner cap is attached the fiber body by a first epoxy.

3. The optical fiber of claim 2, wherein the proximal end of the inner cap includes a surface feature configured to promote adhesion with the first epoxy.

4. The optical fiber of claim 3, wherein an interior surface of the inner cap is spaced part from an exterior surface of the fiber body by the first epoxy to define a sealed interior cavity within the inner cap.

5. The optical fiber of claim 4, wherein the sealed interior cavity includes an insulative element.

6. The optical fiber of claim 5, further comprising one or more attachment points between the interior surface of the inner cap and an exterior surface of the distal end of the fiber body.

7. The optical fiber of claim 2, wherein the proximal end of the outer cap is attached to the inner cap and the fiber body by a second epoxy.

8. The optical fiber of claim 7, wherein the first epoxy has a thermal resistance or elastic modulus different from that of the second epoxy.

9. The optical fiber of claim 7, wherein the second epoxy encapsulates the proximal end of the inner cap and an exterior surface of the first epoxy.

10. The optical fiber of claim 2, wherein the proximal end of the inner cap includes a surface feature configured to promote adhesion with the second epoxy.

11. The optical fiber of claim 1, wherein the one or more openings of the inner cap are proximal of a distal end of the tube.

12. The optical fiber of claim 11, wherein the one or more openings are positioned oppositely along an opening axis transverse with the fiber body.

13. The optical fiber of claim 12, wherein a distal portion of the first flow channel converges toward the one or more openings, and the second flow channel includes an expanded interior portion adjacent the exit port.

14. The optical fiber of claim 1, wherein the inner cap is made of a glass and the outer cap is made of a metal.

15. An optical fiber tip comprising:
   an inner cap including an interior cavity sized to receive an optical fiber, a proximal end engageable with the optical fiber, and at least one transmission portion; and
   an outer cap including an interior cavity sized to receive the inner cap, a proximal end engageable with at least one of the inner cap and the optical fiber, an exit port, and one or more openings,
   wherein, when the inner and outer cap are coupled together, the at least one transmission portion is aligned with the exit port, the outer cap and the inner cap form a flow channel, and the one or more openings are distal of the proximal end of the inner cap.

16. The optical fiber tip of claim 15, wherein the one or more openings extend along an opening axis transverse with the fiber body.

17. The optical fiber tip of claim 15, wherein the second flow channel includes an expanded interior portion adjacent the exit port.

18. The optical fiber tip of claim 15, wherein the proximal end of the inner cap is coupled to the proximal end of the outer cap by an epoxy.

19. The optical fiber tip of claim 15, wherein the inner cap has a thermal resistance greater than a thermal resistance of the outer cap.

20. A laser system including an optical fiber, a laser source, and a fluid source, the optical fiber comprising:
   a fiber body extending between a proximal end engageable with a laser source and a distal end configured to direct laser energy out of the fiber body;
   an inner cap surrounding the distal end of the fiber body, the inner cap including a proximal end attached to the fiber body and at least one transmission portion;
   an outer cap surrounding the inner cap and the distal end of the fiber body, the outer cap including a proximal end attached to the inner cap and the fiber body, and an exit port;
   a tube surrounding at least a portion of the fiber body, the tube including a proximal end engageable with a fluid source and a distal end attached to the outer cap;
   a first flow channel between the tube and the fiber body;
   a second flow channel between the outer cap and the inner cap; and
   one or more openings extending through the inner cap to place the first flow channel in communication with the second flow channel, each of the one or more openings being distal of the proximal end of the inner cap.

* * * * *